US00PP24285P2

(12) United States Plant Patent
Eveleens

(10) Patent No.: US PP24,285 P2
(45) Date of Patent: Mar. 4, 2014

(54) ***ALSTROEMERIA* PLANT NAMED 'TESKANI'**

(50) Latin Name: *Alstroemeria hybrida*
Varietal Denomination: Teskani

(75) Inventor: Peter Eveleens, EW Aalsmeer (NL)

(73) Assignee: VOF Hortipartners, Heerhugowaard (NL)

( * ) Notice: Subject to any disclaimer, the term of this patent is extended or adjusted under 35 U.S.C. 154(b) by 62 days.

(21) Appl. No.: 13/506,951

(22) Filed: May 25, 2012

(51) Int. Cl.
*A01H 5/00* (2006.01)

(52) U.S. Cl.
USPC ..... Plt./309

(58) Field of Classification Search
USPC ..... Plt./309
See application file for complete search history.

*Primary Examiner* — Annette Para
(74) *Attorney, Agent, or Firm* — C. A. Whealy

(57) ABSTRACT

A new and distinct cultivar of *Alstroemeria* plant named 'Teskani', characterized by its upright, somewhat outwardly spreading and uniformly mounded plant habit; sturdy and strong plant form; moderately vigorous growth habit; freely branching habit and relatively short internodes; dense and bushy appearance; large and numerous salmon red and pink-colored flowers held above the foliar plane on relatively short flower pedicels; and good garden performance.

1 Drawing Sheet

Botanical designation: *Alstroemeria hybrida.*
Cultivar denomination: 'TESKANI'.

BACKGROUND OF THE INVENTION

The present invention relates to a new and distinct cultivar of *Alstroemeria* plant, botanically known as *Alstroemeria hybrida*, grown typically as a potted garden *Alstroemeria*, and hereinafter referred to by the name 'Teskani'.

The new *Alstroemeria* plant is a product of a planned breeding program conducted by the Inventor in Heerhugowaard, The Netherlands. The objective of the breeding program is to create new freely-flowering potted garden *Alstroemeria* plants with uniform plant habit and attractive flower coloration.

The new *Alstroemeria* plant originated from a cross-pollination made by the Inventor in Heerhugowaard, The Netherlands in April, 2005 of a proprietary selection of *Alstroemeria hybrida* identified as code number G106, not patented, as the female, or seed, parent with a proprietary selection of *Alstroemeria hybrida* identified as code number PD512, not patented, as the male, or pollen, parent. The new *Alstroemeria* plant was discovered and selected by the Inventor as a single flowering plant from within the progeny of the stated cross-pollination in a controlled greenhouse environment in Heerhugowaard, The Netherlands in February, 2006.

Asexual reproduction of the new *Alstroemeria* plant by root divisions in a controlled greenhouse environment in Heerhugowaard, The Netherlands since April, 2006 has shown that the unique features of this new *Alstroemeria* plant are stable and reproduced true to type in successive generations.

SUMMARY OF THE INVENTION

Plants of the new *Alstroemeria* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Teskani'. These characteristics in combination distinguish 'Teskani' as a new and distinct *Alstroemeria* plant:

1. Upright, somewhat outwardly spreading and uniformly mounded plant habit.
2. Sturdy and strong plant form; moderately vigorous growth habit.
3. Freely branching habit and relatively short internodes; dense and bushy appearance.
4. Large and numerous salmon red and pink-colored flowers held above the foliar plane on relatively short flower pedicels.
5. Good garden performance.

Plants of the new *Alstroemeria* can be compared to plants of the female parent selection. Plants of the new *Alstroemeria* differ from plants of the female parent selection in the following characteristics:

1. Plants of the new *Alstroemeria* have smaller leaves than plants of the female parent selection.
2. Plants of the new *Alstroemeria* and the female parent selection in flower color as plants of the female parent selection have yellow-colored flowers.

Plants of the new *Alstroemeria* can be compared to plants of the male parent selection. Plants of the new *Alstroemeria* differ from plants of the male parent selection in the following characteristics:

1. Plants of the new *Alstroemeria* have shorter flower pedicels than plants of the male parent selection.
2. Plants of the new *Alstroemeria* and the male parent selection in flower color as plants of the male parent selection have pink and white-colored flowers.

Plants of the new *Alstroemeria* can be compared to plants of the *Alstroemeria hybrida* 'Tesrobin', disclosed in U.S. Plant Pat. No. 19,354. In side-by-side comparisons, plants of the new *Alstroemeria* differ primarily from plants of 'Tesrobin' in the following characteristics:

1. Plants of the new *Alstroemeria* have smaller leaves than plants of 'Tesrobin'.
2. Plants of the new *Alstroemeria* and 'Tesrobin' differ in flower color as plants of 'Tesrobin' have red-colored flowers.

BRIEF DESCRIPTION OF THE PHOTOGRAPH

The accompanying colored photograph illustrates the overall appearance of the new *Alstroemeria* plant showing the colors as true as it is reasonably possible to obtain in colored reproductions of this type. Colors in the photograph may differ slightly from the color values cited in the detailed botanical description which accurately describe the colors of the new *Alstroemeria* plant. The photograph comprises a side perspective view of a typical flowering plant of 'Teskani' grown in a container.

DETAILED BOTANICAL DESCRIPTION

The aforementioned photograph and following observations and measurements describe plants of the new *Alstroemeria* plant grown during the winter and early spring in four-liter containers in a glass-covered greenhouse in Kudelstaart, The Netherlands. During the production of the plants, day and night temperatures averaged 12° C. and light levels averaged 7,000 lux. Plants were 21 weeks old when the photograph and description were taken. Color references are made to The Royal Horticultural Society Colour Chart, 2007 Edition, except where general terms of ordinary dictionary significance are used.

Botanical classification: *Alstroemeria hybrida* 'Teskani'.

Parentage:

*Female, or seed, parent*.—Proprietary selection of *Alstroemeria hybrida* identified as code number G106, not patented.

*Male, or pollen, parent*.—Proprietary selection of *Alstroemeria hybrida* identified as code number PD512, not patented.

Propagation:

*Type*.—By root divisions.

*Time to produce a rooted young plant, summer*.—About seven weeks at 20° C.

*Time to produce a rooted young plant, winter*.—About eight weeks at 16° C.

*Root description*.—Fibrous and fleshy; white in color.

*Rooting habit*.—Freely branching; medium density.

*Rhizome length*.—About 3 cm.

*Rhizome diameter*.—About 6 mm.

*Rhizome texture*.—Smooth.

*Rhizome color*.—Close to 195A to 195B.

Plant description:

*Plant and growth habit*.—Herbaceous perennial; upright, somewhat outwardly spreading and uniformly mounded plant habit; broad inverted triangle; freely branching habit with about 13 primary lateral branches developing per plant; relatively short internodes, dense and bushy appearance; sturdy and strong plant form; moderately vigorous growth habit.

*Plant height*.—About 20 cm.

*Plant diameter* (*area of spread*).—About 33.5 cm.

Lateral branch description:

*Aspect*.—Mostly upright to somewhat outwardly spreading.

*Length*.—About 11.8 cm.

*Diameter*.—About 5 mm.

*Internode length*.—About 7 mm.

*Strength*.—Moderately strong.

*Texture*.—Smooth, glabrous; waxy cuticle.

*Color*.—Close to 144A to 144B; waxy cuticle, between 145A and 147D.

Foliage description:

*Arrangement*.—Alternate; below the peduncles in a single whorl; simple.

*Length*.—About 5.6 cm.

*Width*.—About 2.4 cm.

*Shape*.—Ovate; twisting.

*Apex*.—Acute.

*Base*.—Cuneate.

*Margin*.—Entire.

*Texture, upper and lower surfaces*.—Smooth, glabrous.

*Venation pattern*.—Parallel.

*Color*.—Developing leaves, upper surface: Facing downward, close to 137B. Developing leaves, lower surface: Facing upright, close to 138A. Fully expanded leaves, upper surface: Facing downward, between N138B and 189A; venation, close to 144A. Fully expanded leaves, lower surface: Facing upright, between 139A and 147A; venation, close to 144A.

*Petioles*.—Length: About 2.8 cm. Diameter: About 7 mm. Color: Close to 143A; margins, close to 137A.

Flower description:

*Flower type and habit*.—Single zygomorphic flowers arranged in compound umbels; flowers face mostly outwardly to upright; perianth segments separate; freely flowering habit with about twelve flowers developing per inflorescence and about 160 flowers developing per plant.

*Natural flowering season*.—Plants begin flowering about eight weeks after planting; flowering continuous from summer into the autumn in The Netherlands.

*Fragrance*.—None detected.

*Flower longevity on the plant*.—About ten days; flowers not persistent.

*Flower buds*.—Length: About 2.9 cm. Diameter: About 1.3 cm. Shape: Obovate. Color: Close to 143C; distally, close to N137C; base, close to 149C; upper surface of flower bud tinged with between 152A and 177D.

*Umbel height*.—About 10.4 cm.

*Umbel diameter*.—About 13.9 cm.

*Flower diameter* (*horizontal*).—About 6.1 cm.

*Flower length* (*vertical*).—About 6.6 cm.

*Flower depth* (*height*).—About 6.5 cm.

*Perianth*.—Arrangement: Six segments arranged in two whorls, each whorl with two lateral and one median segments. Size, inner perianth: Length, lateral segments: About 6.3 cm. Width, lateral segments: About 2.1 cm. Length, median segments: About 5.6 cm. Width, median segments: About 2.3 cm. Size, outer perianth: Length, lateral segments: About 5.5 cm. Width, lateral segments: About 3.4 cm. Length, median segments: About 6 cm. Width, median segments: About 3.5 cm. Shape, inner perianth, lateral and median segments: Oblanceolate. Shape, outer perianth, lateral and median segments: Obovate. Apex, inner perianth, lateral and median segments: Abruptly acute. Apex, outer perianth, lateral and median segments: Emarginate. Base, inner perianth, lateral and median segments: Narrowly cuneate. Base, outer perianth, lateral and median segments:

Long cuneate. Margin, inner perianth, lateral and median segments: Entire. Margin, outer perianth, lateral and median segments: Towards the apex, finely serrate; towards the base, entire. Texture, inner and outer perianths, lateral and median segments: Smooth, glabrous; slightly velvety. Color, inner perianth: When opening, lateral segments, upper surface: Close to 1D; towards the apex, close to 47A; apex, close to N144D; spots, close to 200D. When opening, median segments, upper surface: Close to 50B; apex, close to N144D; towards the base, close to 50C. When opening, lateral segments, lower surface: Close to 154D; towards the apex, close to 47B; apex, close to N144D; spots, close to 197A. When opening, median segments, lower surface: Close to 51B; apex, close to N144D; towards the base, close to 51D. Fully opened, lateral segments, upper surface: Close to 2D; towards the apex, close to 51A; apex, close to 143B; spots, close to 200D. Fully opened, median segments, upper surface: Close to 51A; apex, close to N144D; towards the base, close to 48B to 48C. Fully opened, lateral segments, lower surface: Close to 2C and 2D; towards the apex, close to 51B to 51C; apex, close to 143A; center, close to 45C; towards the base, close to 35C; spots, close to 197A. Fully opened, median segments, lower surface: Close to 54B to 54C; apex, close to N144D; center, close to 47A to 47B; towards the base, close to 51D. Color, outer perianth: When opening, lateral segments, upper surface: Close to 50A; apex, close to 143A; towards the base, close to N155D. When opening, median segments, upper surface: Close to 50A and 51A; apex, close to 143A; towards the base, close to N155D. When opening, lateral segments, lower surface: Close to 51B; apex, close to 143A; towards the base, close to 56D. When opening, median segments, lower surface: Close to 52B; apex, close to 143A. Fully opened, lateral segments, upper surface: Close to 52B; apex, close to 143A; towards the base, close to 56A to 56B. Fully opened, median segments, upper surface: Close to 52B; apex, close to 143A; towards the base, close to 56C to 56D. Fully opened, lateral segments, lower surface: Close to 52B and 52C; apex, close to 143A; towards the base, close to 52C and 55C. Fully opened, median segments, lower surface: Close to 54B; apex, close to 143A.

*Pedicels*.—Length: About 1.3 cm. Diameter: About 2.5 mm. Strength: Moderately strong. Angle: About 20° from vertical. Texture: Smooth, glabrous; waxy cuticle. Color, upper and lower surfaces: Close to 144A to 144B; waxy cuticle, close to 145A.

*Reproductive organs*.—Stamens: Quantity per flower: Six. Filament length: About 3.9 cm. Filament color: Close to 51B. Anther shape: Reniform. Anther length: About 2 mm. Anther color: Close to 152A to 152B. Pollen amount: Moderate. Pollen color: Close to 201A. Pistils: Quantity per flower: One. Pistil length: About 4 cm. Style length: About 3.6 cm. Style color: Close to 51B; towards the base, close to 51C. Stigma shape: Tri-parted; parts, club-shaped, curved. Stigma color: Close to 49C to 49D. Ovary color: Close to 144A.

*Fruits and seeds*.—Fruit and seed development have not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have good garden performance and to tolerate wind, rain, high temperatures of about 35° C. and to be hardy to USDA Hardiness Zone 8.

It is claimed:

1. A new and distinct *Alstroemeria* plant named 'Teskani' as illustrated and described.

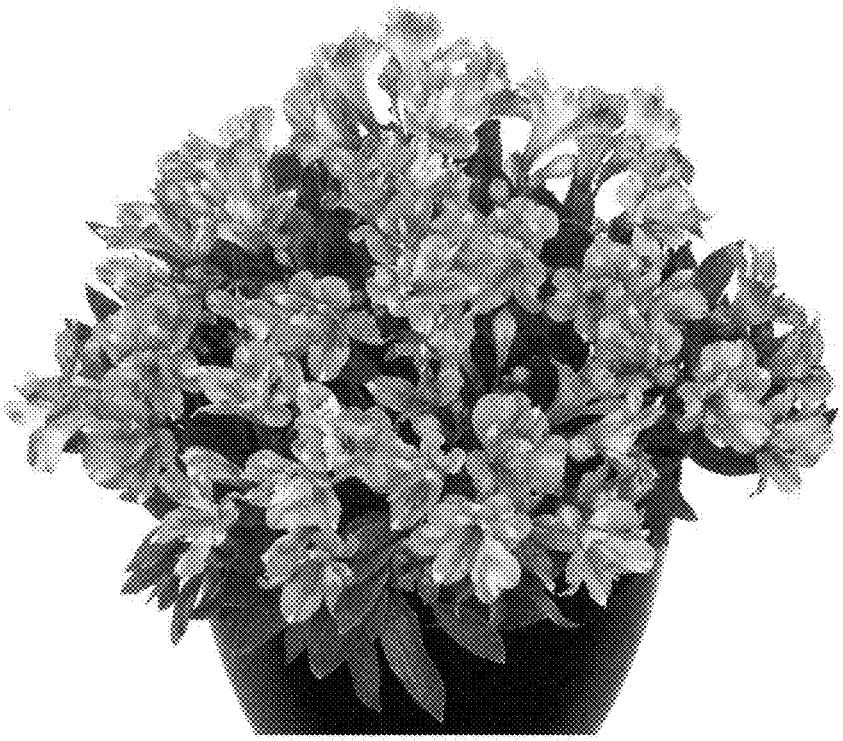

* * * * *